United States Patent [19]

Haystead

[11] Patent Number: 5,536,822

[45] Date of Patent: Jul. 16, 1996

[54] γ-PHOSPHATE LINKED ADENOSINE 5' TRIPHOSPHATE SEPHAROSE

[75] Inventor: Timothy A. J. Haystead, Charlottesville, Va.

[73] Assignee: University of Virginia Alumni Patents Foundation, Charlottesville, Va.

[21] Appl. No.: 207,632

[22] Filed: Mar. 9, 1994

[51] Int. Cl.$^6$ .............................. C07H 19/20; C12N 9/12; B01D 15/08

[52] U.S. Cl. ...................... 536/26.26; 435/194; 435/815; 210/690; 210/691; 210/692

[58] Field of Search .................................. 435/194, 815; 210/690, 691, 692; 514/45; 527/303, 312; 536/26.26

[56] References Cited

PUBLICATIONS

Haystead et al, Eur. J. Biochem. 214 (2): 459–467 (1993).
Berglund et al, Eur. J. Biochem. 28: 492–496 (1972).
"Affinity Chromatography, Principles and Methods" Published by Pharmacia Fine Chemicals (1974).

Primary Examiner—John W. Rollins
Assistant Examiner—Francisco C. Prats
Attorney, Agent, or Firm—Oblon, Spivak, McClelland, Maier & Neustadt

[57] ABSTRACT

A γ-phosphate-linked ATP affinity column for the purification of a protein kinase is provided. In addition, a method for purifying protein kinases using the γ-phosphate-linked ATP affinity column comprising the steps of 1) linking an ATP linking moiety to an affinity column via the γ-phosphate position of ATP; 2) applying a sample of protein kinase to the γ-phosphate linked ATP solid support so as to bind the protein kinase to the γ-phosphate-linked ATP; 3) washing the bound support with a salt which will not affect the binding of the bound protein kinase; and 4) eluting the bound protein kinase with an ATP salt so as to obtain homogenous protein kinase is provided.

7 Claims, 9 Drawing Sheets

STRUCTURE OF γ– PHOSPHATE LINKED ATP SEPHAROSE

USE OF γ-PHOSPHATE LINKED ATP SEPHAROSE.

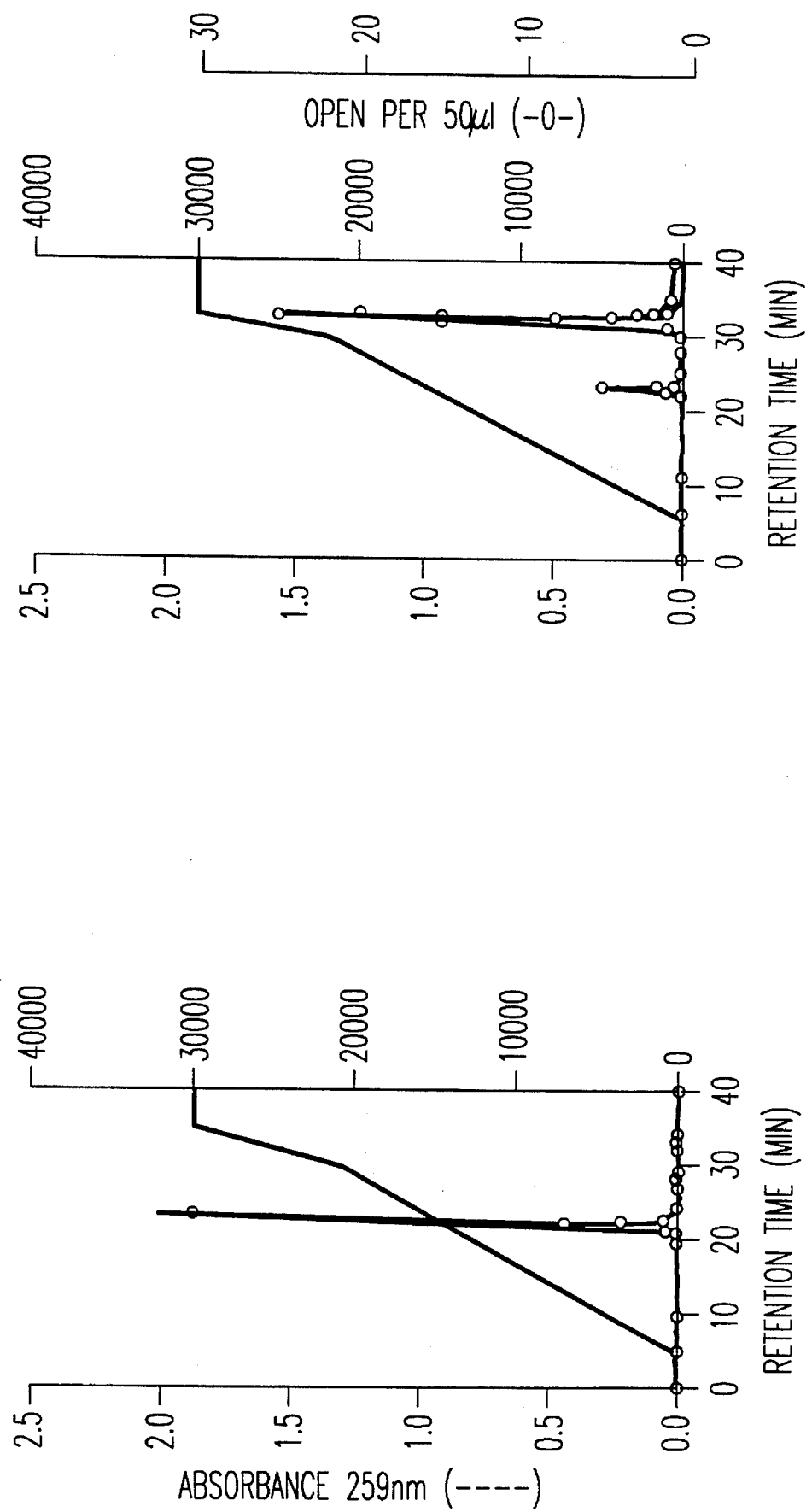

γ-PHOSPHATE LINKED ADENOSINE 5' TRIPHOSPHATE SEPHAROSE

BACKGROUND OF THE INVENTION

1. Field of the Invention

The invention relates to a γ-phosphate linked adenosine 5' triphosphate (ATP)-Sepharose affinity column for the purification of protein kinases and a method for using the affinity column to purify protein kinases.

2. Background of the Invention

Protein kinases are enzymes capable of phosphorylating certain amino acid residues in specific proteins. For example, the breakdown of glycogen is regulated by protein kinases. Specifically, when adrenaline binds to the liver cell, cyclic adenosine monophosphate (AMP) is produced which promotes the activation of cyclic AMP dependent protein kinase. Phosphorylation of the active form of glycogen synthase (dephospho) by cyclic AMP protein kinase converts the enzyme to its phosphorylated, inactive form. The transformation of glycogen synthase to its phosphorylated form allows for the breakdown of glycogen to glucose to be used for energy. Cyclic AMP dependent protein kinase further catalyzes the phosphorylation of the inactive phosphorylase kinase by ATP to yield the active, phosphorylated form of phosphorylase kinase.

Protein kinases are allosteric enzymes. Cyclic AMP dependent protein kinases represent a typical example of this group of enzymes. The inactive forms contain two catalytic subunits and two regulatory subunits. When the subunits are associated together in a complex, the enzyme is inactive. However, when cyclic AMP binds to the sites of the two regulatory subunits, the protein kinase becomes enzymatically active. When the protein kinase is activated, the enzyme can phosphorylate a number of other enzymes in different kinds of target cells.

Therefore, the process of protein phosphorylation is recognized as a fundamental mechanism by which regulation of many important cellular processes is achieved.

Extensive research has been devoted to the characterization of protein kinases which catalyze protein phosphorylation, due to the linkage of many of these enzymes with diseases such as cancer and diabetes. The enzymes may also be of agricultural and industrial importance since several protein kinases have been identified which regulate plant, yeast and bacterial metabolism in, for example, rapeseed oil synthesis, brewing, and antibiotic synthesis.

Protein kinases can be categorized into three distinct classes, based on the amino acids they phosphorylate. These are the serine/threonine protein kinases, eg. cyclic AMP-dependent protein kinase (Walsh et al. (1968) *J. Biol. Chem.*, 243:3763–3765; Taylor et al. (1990) in *Peptides and Protein Phosphorylation*, (Kemp, B. E. ed) pp. 2–32, CRC Press) or mitogen-activated protein (MAP) kinase (Sturgill et al. (1991) *Biochem. Biophys. Acta.*, 1092:350–357); the tyrosine protein kinases, eg. $p60^{c-arc}$ (Anderson et al. (1985) *Mol. Cell. Biol.*, 5:1122–1128; Martinez et al. (1987) *Science*, 237: 411–415); and the recently discovered dual specificity protein kinases that phosphorylate exogenous substrates on both tyrosine and serine/threonine amino acids, eg. MAP kinase kinase (MAPKK) (Ahn et al. (1991) *J. Biol. Chem.*, 266:4220–4227; Gomez et al. (1991) *Nature*, 353:170–175; Crews et al. (1992) *Science*, 258: 478–480; Seger et al. (1992) *J. Biol. Chem.*, 267:25688–25631; Seger et al. (1992) *J. Biol. Chem.*, 267:14373–14381; Nakielny et al. (1992) *FEBS Lett.*, 308:183–189; Ashworth et al. (1992) *Oncogene*, 7:2555–2556; Wu et al. (1992) *Biochem, J.* 285: 701–705.

However, despite the growing interest in protein kinases, to date, no direct methods have existed for the affinity purification of protein kinases.

Past attempts to purify protein kinases have resulted in relatively poor purification steps. ATP columns such as ATP-agarose have been used in many protein kinase purification protocols.

However, typically these columns have been constructed by coupling the nucleotide to a solid matrix, either through the N6 amino group on the purine ring or hydroxyl groups of the ribose moiety {Trayer et al. (1974) *Biochem. J.*, 139:609–623; Jeno, P. and Thomas, G (1991) *Methods Enzymology Zoo:* 178–187. However, based on the orientation of MgATP within the catalytic cleft of cyclic A kinase, previous ATP columns were unlikely to act as true affinity steps in the purification of most, if not all, protein kinases. The reason is that the purine rings are buried in a hydrophobic pocket, sterically precluding affinity purification by linkage through these moieties. Linkage via the ribose hydroxyl groups is also likely to be sterically hindered from viewing the structure of cyclic A kinase.

Thus, previous ATP columns have functioned for the most part as weak cation-exchange resins and not as a specific affinity ligand for protein kinases.

Further, although purification of up to twenty-fold has been obtained in a few cases (e.g., 70–kDa ribosomal S6 kinase described in Jeno et al. (1989) *J. Biol. Chem.*, 264:1293–1297; Jeno et al. (1991) *Methods Enzymol.*, 200:178–187), with such columns, adsorption requires low ionic strength, suggesting binding of protein kinases by ionic interactions only.

Therefore, a more effective means of immobilizing ATP is needed in order to provide a means for purification of protein kinases.

SUMMARY OF THE INVENTION

An object of the present invention is to provide a more effective means of immobilizing ATP to be used to purify protein kinases.

In addition, it is an object of the present invention to provide a method for purification of protein kinases using a means which more effectively immobilizes ATP.

The previously mentioned objects have been met by the present invention which provides a γ-phosphate linked adenosine 5' triphosphate affinity column for the purification of protein kinases. The above objects have further been met by a method for purifying protein kinase by applying protein kinase extracts to an affinity column containing γ-phosphate linked adenosine 5' triphosphate, washing with a salt, and specifically eluting the purified protein kinases from the column with an ATP salt wash.

BRIEF DESCRIPTION OF THE DRAWINGS

FIG. 4(A)–FIG. 4(D) are graphs of absorption versus retention time in an analysis of synthesis of adenosine-5'-(γ-4-nitrophenyl) triphosphate from ATP by reverse phase HPLC.

DETAILED DESCRIPTION OF THE INVENTION

Figure 1:
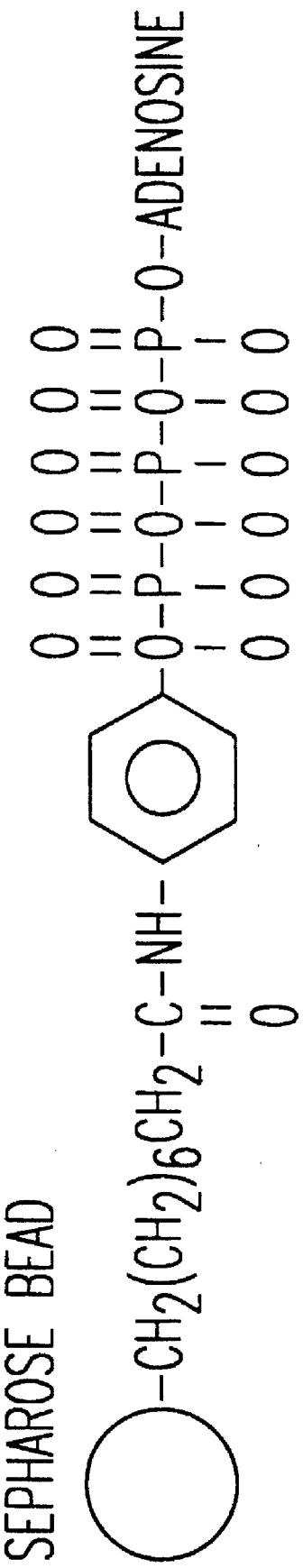
FIG. 1 is the structure of γ-phosphate linked ATP Sepharose.

The present invention will now be described more fully hereinafter with references to the accompanying drawings, in which preferred embodiments of the invention are shown. This invention can, however, be embodied in many different forms and should not be construed as limited to the embodiments set forth herein; rather, Applicant provides these embodiments so that this disclosure will be thorough and complete, and will fully convey the scope of the invention to those skilled in the art.

The present invention provides a γ-phosphate-linked adenosine 5' triphosphate affinity column for the purification of protein kinases, along with a method for purifying protein kinases using such a column.

Specifically, the present invention provides an affinity column for purification of a protein kinase comprising:

a) a solid support; and
b) a linking moiety linked to said solid support, wherein said linking moiety has the following formula I:

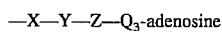

—X—Y—Z—Q$_3$-adenosine wherein X is a straight or branched chain having at least 2 carbon atoms and is suitable for covalently linking —Y—Z—Q$_3$ adenosine to said solid support; Y is selected from the group consisting of an amino, nitro, hydroxy, and disulfo group; Z is a substituted or unsubstituted phenyl group; and Q is phosphate or thiophosphate.

X can be any straight or branched chain having at least 2 carbon atoms and is capable of covalently linking —Y—Z—Q$_3$-adenosine to the solid support. X is preferably a straight or branched C$_1$–C$_{20}$, preferably C$_2$–C$_9$, alkyl, alkenyl, or alkynyl chain. X may be substituted or unsubstituted. X can be substituted with an amine, halogen, nitro, hydroxy, sulfhydryl or carboxyl group. Examples of X include an aldehyde such as formaldehyde, acetaldehyde, propanal, butanal, pentanal, hexanal, heptanal, octanal, nonanal, etc.; an amino-substituted alkyl such as ethylene diamine, propane diamine, butane diamine, pentane diamine, hexane diamine, heptane diamine, octane diamine, nonane diamine, etc.; a halogen-substituted alkyl such as chloromethane, fluoromethane, bromomethane, etc., dichloromethane, difluoromethane, dibromomethane, etc., trichloromethane, trifluoromethane, tribromomethane, etc., chloroethane, fluoroethane, bromoethane, etc., dichloroethane, difluoroethane, dibromoethane, etc.; nitromethane, nitroethane, nitropropane, etc.; hydroxymethane, hydroxyethane, hydroxypropane, etc.; dimethyl disulfide, diethylsulfide, etc; acetone, butanone, pentanone, etc. Preferably, X is a compound which provides an aldehyde linkage to —Y—Z—Q$_3$-adenosine. Particularly preferred is nonanal.

Y is an organic group such as amino, nitro, hydroxy, or disulfo group. Y is preferably an amino or nitro group.

Z is a substituted or unsubstituted phenyl group. The phenyl substituents can be halogen, alkyl, nitro, amine, hydroxy, sulfhydryl, carboxyl, etc. For example, Z can be phenylene, phenol, nitrophenol, dinitrophenol, phenylbromide, phenylchloride, phenylethane, etc. Z is preferably phenylene.

Q can be either a phosphate or thiophosphate group. Preferred is a phosphate group.

The linking moiety (Y—Z—Q) of the present invention is preferably adenosine-5'-(γ-4-nitrophenyl)triphosphate or adenosine-5'-(γ-4-hydroxyphenyl)triphosphate. FIG. 1 specifically depicts adenosine-5'-(γ-4-aminophenyl) triphosphate-Sepharose. ATP can be replaced with ATP-γ-S which provides for thiophosphates in place of the phosphate groups of ATP. Although the description that follows and examples use the preferred phosphate groups, the invention encompasses use of triphosphate in place of these phosphate groups.

Any affinity substrate can be used as the solid matrix in the present invention, including, but not limited to, Sepharose, agarose gels, cross-linked agarose gels, controlled-pore glass (CPG) beads, cellulose particles, polyacrylamide gel beads, polyacrylamide gel beads, and Sepharose gel beads.

In FIG. 1, ATP is chemically linked through the linking moiety to the solid support (Sepharose bead) at its γ-phosphate position. Chemical linkage to other functional moieties, such as the α or β position, would sterically preclude binding of protein kinases to immobilized ATP.

Figure 3:
FIG. 3 is a stereoview of the active site of the catalytic subunit of cyclic-AMP-dependent protein kinase with bound MnATP.

Specifically, it is clear from FIG. 3 that the adenine portion of ATP is buried deep within a conserved hydrophobic pocket of the catalytic cleft of the kinase, with the α,β and γ phosphates oriented to the opening of the cleft (FIG. 3). In addition to hydrophobic interactions, hydrogen-bond contacts are formed with the enzyme and the N6 amino group and N7 nitrogen atoms of the adenine ring. The 2-position and 3-position hydroxyl groups of the ribose rings are also directly involved in hydrogen-bond formation with the enzyme. The α phosphate is anchored by Lys 72 and Glu 91 and the β-phosphate oxygen interacts with the main-chain amides of the conserved glycinerich loop. Invariant amino acids, Asp 184 and Asn 171, are found to chelate Mg$^{2+}$ to secure the γ phosphate at the mouth of the catalytic cleft.

Therefore, ATP has been effectively immobilized by linkage through its γ-phosphate group for the first time by the present inventor.

Figure 2:
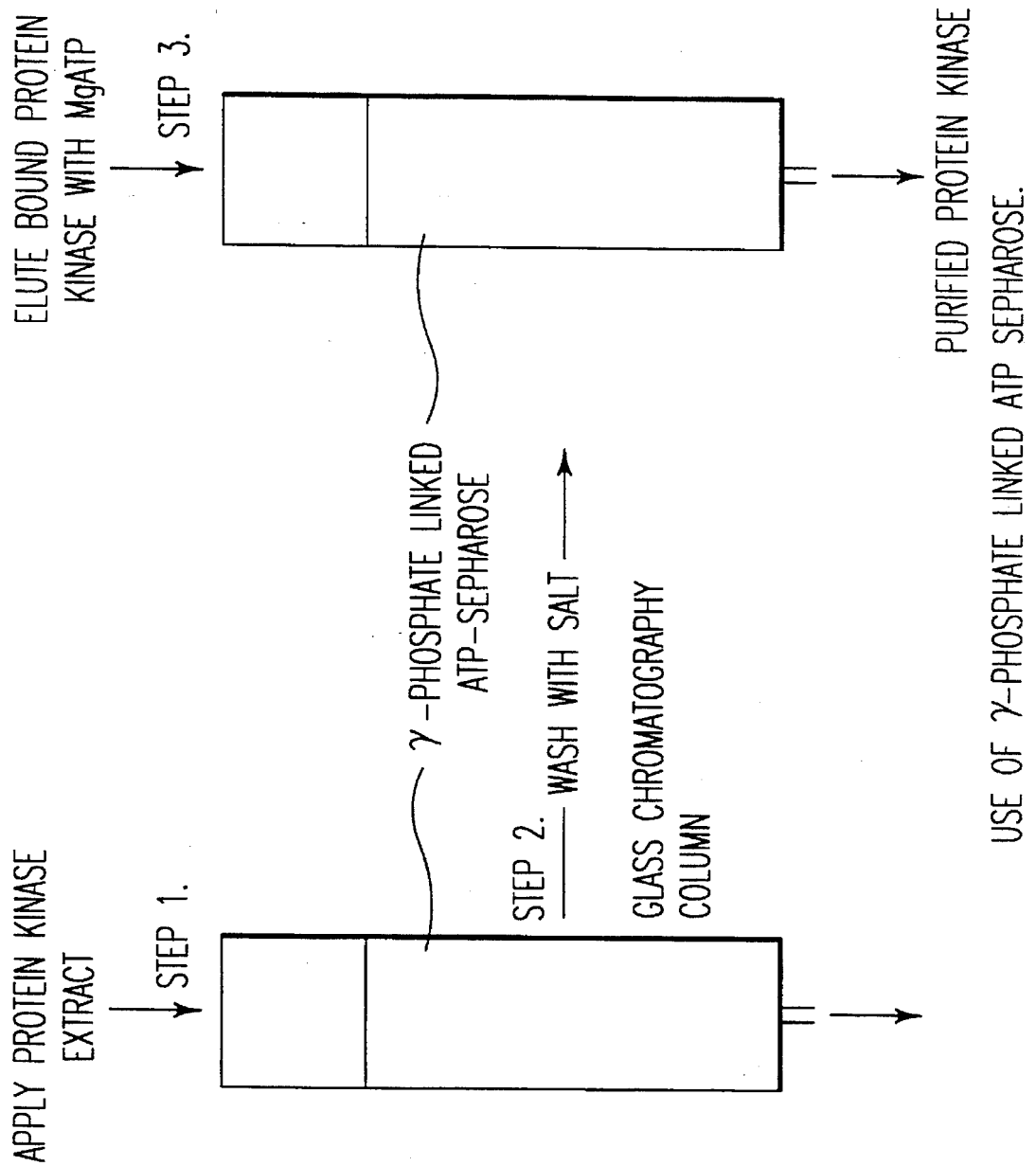
FIG. 2 is a diagram showing the method of use of the γ-phosphate linked ATP Sepharose.

FIG. 2 demonstrates the use of the γ-phosphate linked ATP Sepharose in affinity purification of protein kinases. In step 1, protein kinase extracts are applied to a solid support which is chemically linked to ATP through its γ-phosphate position. Step 2 involves washing the column with a salt which will not affect the binding of the γ-phosphate-linked ATP to the column, and Step 3 involves eluting the bound protein kinase with an ATP salt (MgATP) to obtain purified protein kinase.

Any protein kinase can be purified by use of the disclosed γ-phosphate-linked ATP affinity column and by use of the disclosed method for purifying protein kinases using the affinity column. The present invention uses the ternary complex of cAMP-dependent protein kinase (cyclic A kinase), an ATP salt and a 20-residue inhibitor peptide.

Many invariant amino acids and conserved hydrophobic residues participate in the binding and orientation of MgATP, or other ATP salts, for catalysis. It has been observed that eleven highly conserved subdomaines exist within the catalytic domain of all protein kinases. Fifteen amino acid residues within the eleven conserved subdomaines of all protein kinases appear to be nearly invariant. In addition to the invariant residues, several hydrophobic amino acids of similar structure are also conserved within the protein kinase family. The positioning of the invariant and conserved hydrophobic amino acids within the primary structure of all protein kinases suggests a structural feature common to all of the protein kinase enzymes. Specifically, as shown in FIG. 3, eight of the nearly invariant amino acids found in all protein kinases form direct interactions with the nucleotide. In view of the degree of conservation of residues within the catalytic core of all protein kinases, and in view of the binding site with ATP, the binding and orientation of the ATP salt is probably the same for all protein kinases.

Therefore, any protein kinase can be purified according to the present invention including, for example, serine\threonine protein kinases (eg, cyclic AMP-dependent protein kinase or mitogen-activated-protein (MAP) kinase; the tyrosine protein kinases (eg., $p60^{c-src}$); "dual specificity" protein kinases that phosphorylate exogenous substrates on both tyrosine and serine\threonine amino acids (eg., MAP kinase kinase (MAPKK), p. $42^{mapk}$; and further, the 65 protein kinases disclosed in Hanks et al., (1988) *Science*, 241:42–52, and Hanks et al. (1991) *Methods Enzymol.*, 200:38–62. Therefore, the present invention is useful for purifying all known protein kinases and any protein kinases in which it is determined that the structure includes homology to cyclic A kinase at its ATP binding sites.

The salt used in Step 2 includes any salt which does not affect the binding of the γ-phosphate-linked ATP to the column, and which does not affect the binding of the protein kinase thereto. Salts such as Hepes, dithiothreitol, EDTA, tris, EGTA, 2-glycerophosphate, NaCl, kemptide or a mixture thereof, are useful in Step 2 of the method of the present invention.

The amount of the salt used in the present invention is from 1–150, preferably 20–50 mM.

An ATP salt such as AMP (5'adenosine monophosphate), ADP (adenosine diphosphate), MgATP, MgADP, MgAMP, MnATP, MnADP, MnAMP, NaATP, NaADP, NaAMP, $K^+$ATP, $K^+$ADP, $K^+$AMP, or mixtures thereof, are used to elute the bound protein kinase.

The amount of the ATP salt useful in eluting the bound protein kinase is in the range of 0.1 to 10 mM. The preferred range of ATP salt is 1 to 10 mM.

The coupling method used depends upon the nature of the column used. In the present invention, it is preferred to link ATP—Z—Y—X to Sepharose by the carbodimide reaction. A variety of coupling methods for attaching ligands to the support can be used. ATP is linked to the solid support though its γ-phosphate position by covalently bonding ATP to the linking moiety —X—Y—Z— and passing this resulting solution over the solid support. The ATP—Z—Y—X compound can be mixed with a buffer such as water before being passed over the solid support. The ATP—Z—Y—X compound can be mixed with a buffer such as water before being passed over the solid support.

After the column is prepared, partially purified protein kinase can be applied to the solid support at a flow rate of 0.1 to 10 ml per minute.

The amount or presence of the protein can be determined, for example, by the method disclosed in Bradford, M.M. (1976) *Anal. Biochem.* 72, 248–254. Other methods can be used for protein determinations, such as absorbance at 280 nMs in a spectrophotometer.

The details of the mechanism of reaction of the γ-phosphate linked ATP affinity column purification of protein kinases as herein described reside in the fact that the γ-phosphate ATP linking moiety competes with ATP, and that the presence of an —Z—X— or other appropriate moiety linked to the γ-phosphate, does not adversely affect binding of the nucleotide to these enzymes. This is consistent with ATP binding to cyclic-A kinase, as shown in FIG. 3, in which the γ-phosphate is oriented and exposed at the opening of the catalytic cleft.

By use of the present invention, protein kinases can be purified to over 19,000-fold homogeneity. Using previously known purification schemes, purification of up to only 20-fold has been obtained (Jeno et al., (1989) *J. Biol. Chem.*, 264:1293–1297; and Jeno et al. (1991) *Methods Enzymol.*, 200:178–187).

The effectiveness of the present invention can be improved by partially purifying the protein kinases prior to application of the extracts to the ATP affinity column of the present invention. This allows for the protein kinases to be enriched, but not homogeneous. Also, the ability of the claimed column to bind protein kinases can be significantly improved by introduction of a C6 carbon spacer between the Sepharose beads and the ligand.

The invention will be further explained in the following examples. However, the examples are for purposes of illustration only, and are not intended to limit the scope of the subject matter of the present invention.

EXAMPLES

Example 1

[γ-$^{32}$P] ATP was synthesized according to the procedure set forth in Johnson et al., *Advances in Cyclic Nucleotide Research*, 10:135–167 (1979). The catalytic subunit of cyclic-AMP-dependent protein kinase was purchased from Promega. $p60^{c-src}$ was obtained from the Department of Microbiology, University of Virginia. Recombinant $p42^{mapk}$ was purified as described in Haystead et al., (1992) *FEBS Lett.*, 306:17–22. STE7 antibody was obtained from the University of Vancouver, Canada.

Synthesis of adenosine-5'-(γ-4-aminophenyl)triphosphate-Sepharose.

In order to synthesize adenosine-5'-(γ-4-aminophenyl) triphosphate, 1 g disodium salt of [γ-$^{32}$P]ATP (100 cpm/nmol) was dissolved in 20 ml 100 mM Et$_3$NHCO$_c$ (solution A) and passed over a 15 cm×2.5 cm column of cation-exchange resin (AG 50W-X8, Bio-Rad) previously equilibrated in solution A. The column was washed with 250 ml of solution A and the eluate evaporated. The residue was dissolved in 20 ml methanol/water (1:1), 3 mM tri-n-ethylamine was added and the solution evaporated. The residue was dissolved in dry methanol, evaporated, and this procedure was repeated twice more. The residue was dissolved under argon in 2 ml dry methanol and 8 ml dry dimethylformamide. Dicyclohexyl carbodiimide was added (5 mM) and formation of the adenosine-5'-trimetaphosphate monitored by reverse-phase HPLC. The results are shown in FIG. 4(A) and 4(B).

FIG. 4(A) shows the retention time of triethyl ammonium salt of [γ-$^{32}$P]ATP versus absorbance. FIG. 4(B) demonstrates the products after reaction of ATP with dicyclohexyl carbodiimide for 180 minutes. Adenosine-5'-trimetaphosphate elutes at 32.00 minutes. In all cases, 45 pmol was applied to a 10 cm×0.8 cm Radial Pak $C_{18}$ column (Waters) equilibrated in 100 mMsolution A. The column was developed with an indicated gradient of acetonitrile/100 mM solution A at a flow rate of 1.0 ml/min. The absorbance was monitored at 259 nm and the radioactivity was determined by scintillation counting of 50 μl aliquotes of (1.0 ml) column fractions.

Figure 4D:
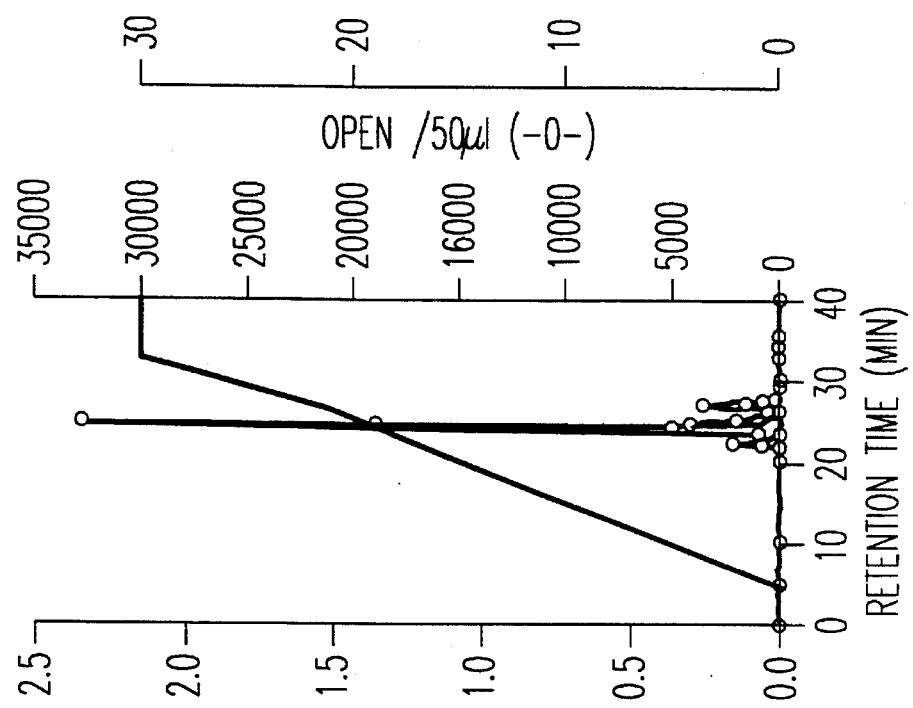
Figure 4C:
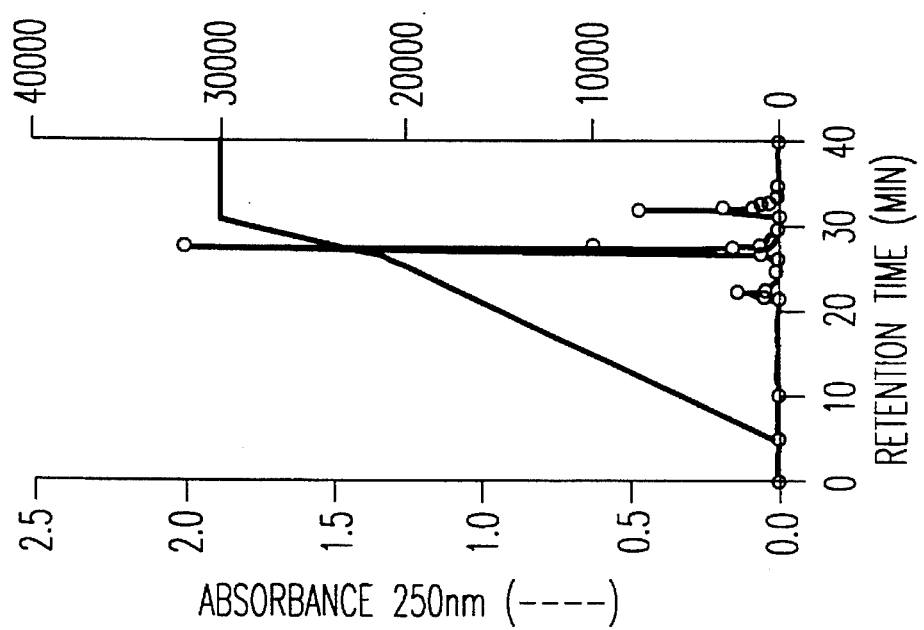

Following conversion to adenosine-5'-trimetaphosphate [FIG. 4(B)], 2.0 ml dry pyridine was added and the mixture evaporated. The residue was dissolved under argon in 10 ml dry dimethylfluoride, 20 mM 4-nitrophenyl and20 mM tri-n-ethylamine. The yellow solution (with dicyclohexyl carbodiimide precipitate) was kept at approximately 25° C. for 20 hours and an aliquot of the reaction products analyzed by HPLC (FIG. 4C). FIG. 4(C) shows the products after reaction of adenosine-5'-trimetaphosphate with p-nitrophenol for 16 h, forming adenosine-5'-(γ-4-nitrophenyl) triphosphate. The major product, eluting at 27.00 min, had a molecular mass of 627 daltons as determined in a Finnigan triplequadrapole electrospray mass spectrometer. This is consistent with the reaction of 4-nitrophenol with adenosine-5'-trimetaphosphate to form adenosine-5'-(γ-nitrophenyl) triphosphate. The identity of the product was further confirmed by scanning spectrophotometric analysis, which revealed two absorbance maxima (γ-nitrophenyl) triphosphate at 280 nm and 259 nm, consistent with the presence of a phenolic and adenyl moiety.

The product was added to 50 ml water and evaporated to remove tri-n-ethylamine. The residue was dissolved in 100 ml $H_2O$, adjusted to pH 5.0 with acetic acid, and extracted three times with ether. The water phase was evaporated to 20 ml and adjusted to pH 9.0 with ammonia and adenosine-5'-(γ-4-nitrophenyl)triphosphate purified by DEAE anion-exchange chromatography. The column (2.5 cm×60 cm) was equilibrated in 100mM of solution A and developed with a 3000-ml linear gradient of 0.1M solution A to 1M. Column fractions showing absorbance at 259 nm were pooled and evaporated.

Approximately 1.5 mM adenosine-5'-(γ-4-nitrophenyl)-triphosphate was dissolved in 15 ml water and 400 mg palladium-activated carbon (10% palladium, by mass.) added. Hydrogenolysis was carried out at atmospheric pressure until >95% (4-6h) of the 4-nitrophenol derivative had been converted to adenosine-5'-(γ-4aminophenyl)triphosphate (FIG. 4D). Mass spectrometry of the major product identified by HPLC yielded a molecular mass of 597 daltons, consistent with the reduction of adenosine-5'-(γ-4-nitrophenyl)triphosphate to adenosine-5'-(γ-4-aminophenyl)triphosphate. Following hydrogenolysis, the carbon was removed by filtration. The product, adenosine-5'-(γ-4-aminophenyl)triphosphate, was purified by DEAE anion-exchange chromatography as described above. Column fractions showing absorbance at 259 nm were pooled, evaporated and desalted by co-evaporation three times with methanol. The product (yield ≈80%) was resuspended in 20 ml water and stored at −20° C. until required.

An amount of 100 ml settled CnBr-activated Sepharose 4B was prepared as described by Cuatrecasas et al. (1971) *Annu. Rev. Biochem.*, 40:259. The washed Sepharose was suspended in 100 ml 2M 1,6-diaminohexane, pH 10, for 16 h at 4° C. The Sepharose was washed extensively, suspended in 100 ml distilled water and pulverized succinic anhydride (1 mM/ml gel). After mixing, the suspension was kept at pH 6.0 by continuous addition of 5M NaOH. After the pH was stable, the gel was mixed by rotation overnight at 4° C. The gel was washed extensively with 0.1M NaOH and distilled water and [γ-$^{32}$P]adenosine-5'-(γ-4-aminophenyl) triphosphate (52 μmol/ml gel) coupled to the Sepharose by carbodiimide reaction for 24 hours at 25° C. The resin was washed extensively with solution B (50 mM 2-glycerophosphate, pH 7.3, room temperature, 1 mM dithiothreitol, 1.5 mM EGTA) containing, additionally 1M NaCl. The resin was equilibrated and stored in solution B containing 0.2% sodium azide.

The efficiency of coupling was determined by measuring the amount of radioactivity incorporated/ml settled Sepharose, and also, by analytical reverse-phase HPLC of the eluate from the carbodiimide reaction. It was calculated that 6–8 μmol [γ-$^{32}$P]adenosine-5'-(γ-4-aminophenyl)triphosphate was coupled/ml settled Sepharose.

The results can be improved by passing crude muscle extract over the column, washing with high salt, then 10 mM ATP. This column treatment was found to improve yields of protein kinases, presumably by blocking non-specific hydrophobic binding sites.

Example 2

Figure 5B:
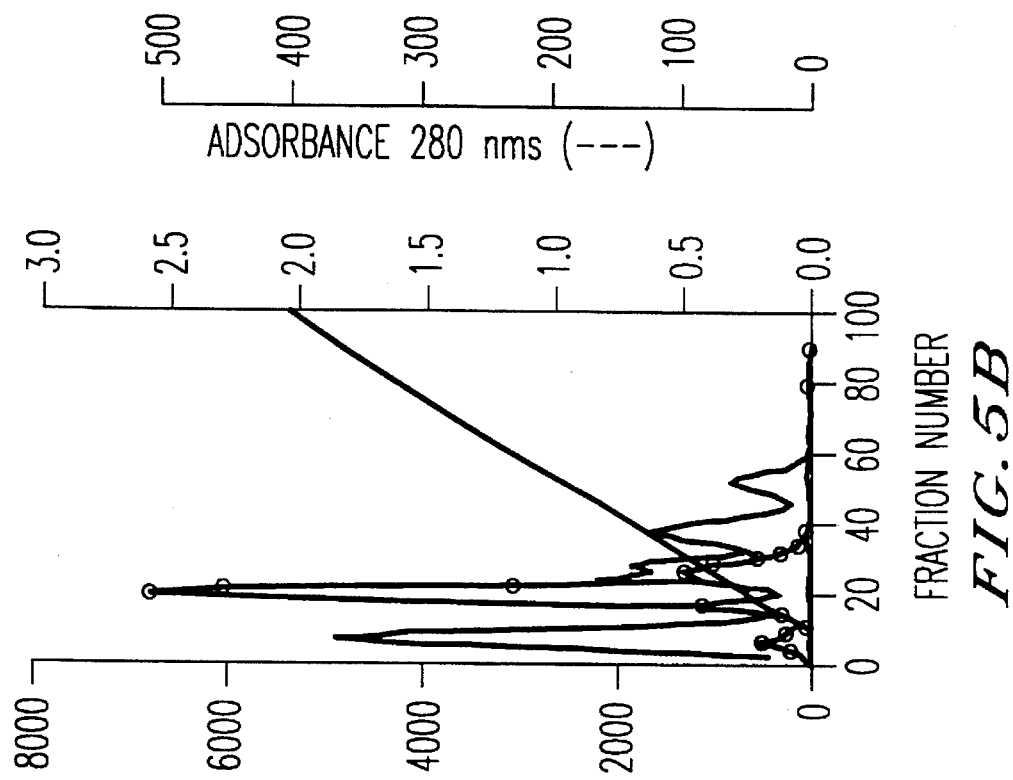
FIG. 5(A)–FIG. 5(B) are graphs of an anion-exchange gel-filtration chromatography of mitogen-activated protein kinase kinase (MAPKK) showing MAPKK activity versus fraction number.
Figure 5A:
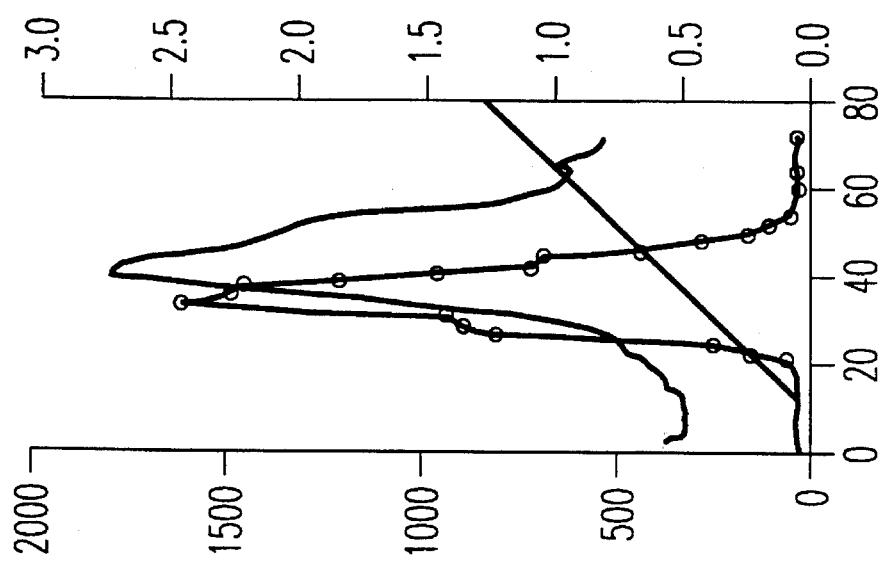
Figure 5C:
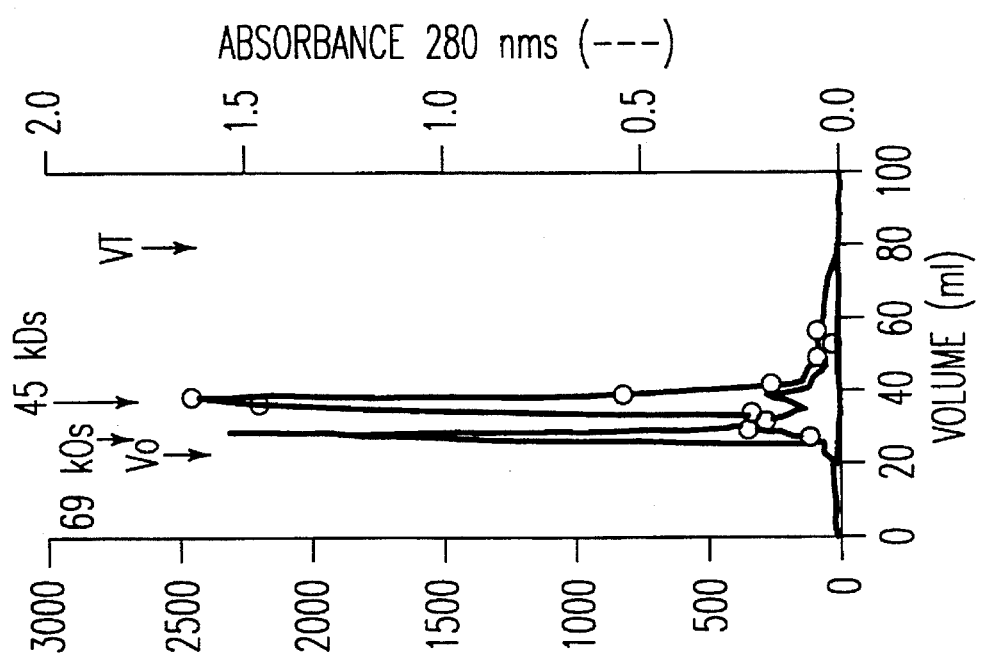
FIG. 5(C) is also a graph of an anion-exchange and gel-filtration chromatography of MAPKK showing MAPKK activity versus volume.

Preparation of rabbit skeletal muscle MAPKK for adenosine-5'-(γ-4-aminophenyl)triphosphate affinity chromatography A fed female New Zealand white rabbit was euthanized by lethal injection with phenobarbital via the marginal ear vein. The back and hind-limb skeletal muscle (300 g) were rapidly excised, minced and homogenized at 4° C. with 2.5 vol. solution C (50 mM 2-glycerophosphate, pH 7.3, 1.5 mM EGTA, 0.15 μM sodium orthovanidate, 1 mM dithiothreitol, 1 mM phenylmethanesulfonyl fluoride, 1 mM benzamidine) containing 6 μg/ml leupeptin. All subsequent steps were carried out at 4° C. The homogenate was centrifuged at 6000 ×g for 45 minutes and the supernatant mixed for 3 h with 500 ml settled DEAE cellulose (Watman), previously equilibrated in solution C (50 mM 2-glycerophosphate, PH of 7–3, 1.5 mM EGTA, 0.15 mM orthovanidate, 1 mM dithiothreitol, 1 mM PMSF, 1 mM Benzamidine). The DEAE was packed into a glass column (20 cm×50 cm) washed with solution C until the absorbance at 280 nM of the eluate was <0.005 absorbance. The column wash (≈41) was adjusted to pH 8.8 with NaOH and centrifuged at 6000 ×g for 45 min. The supernatant was applied to a FFQ Sepharose column (10 cm×50 cm), equilibrated in solution C, pH 8.8. After washing extensively, the column was developed with a 3000-ml linear salt gradient to 1M NaCl [FIG. 5(A)]. Column fractions containing MAPKK were diluted 50-fold in solution C, pH 7.3, prior to assay. (3×2-1 changes) The dialysate was centrifuged (40000 ×g) for 45 min. and applied to a Waters AP-1Q column (0.8 cm×10 cm) equilibrated in solution C, pH 7.3, and developed with the indicated salt gradient to 400 mM at a flow rate of 1.0 ml/minute. Fractions were diluted 100-fold in solution C, pH 7.3, prior to assay. (FIG. 5B). The major peak of MAPKK activity was pooled and concentrated by ammonium sulfate precipitation (45%, mass/vol.). The enzyme was resuspended in 0.5 ml solution C, pH 7.3, and applied to a G75 superfine gel-filtration column (0.5 cm×100 cm), equilibrated in solution C, pH 7.3, containing 150 mM NaCl (FIG. 5C). Fractions of 250 μl concentrated MAPKK were applied to the column and developed at a flow rate of 0.1 ml/min. Molecular mass markers are bovine serum albumin (69 kDa) and ovalbumin (45 kDa). Column fractions containing MAPKK activity were pooled and affinity purified over adenosine-5'-(γ-4-aminophenyl)triphosphate-Sepharose.

Example 3

Protein kinase assays

The 42-kDa MAP kinase (p42$^{mapk}$) and MAPKK were assayed as described previously (Haystead et al. (1992) *FEBS. Lett.*, 306:17–22). The cyclic-A kinase assays (30 μl) included 1 μg cyclic-A kinase, 2 mM Kemptide, 50 mM Hepes, pH 7.4, 1 mM dithiothreitol, 200 μM ATP, 5 mM MgCl$_2$. Reactions were terminated by spotting 25 μl assay mixture onto P81 paper as described in Haystead et al. (1992) *FEBS Lett.*, 306:17–22. p60$^{c-arc}$ assays were similar, except a 2 mM peptide (Rossomando et al., 1992) *Proc. Natl. Acad. Sci.*, 89:5221–5225) was used as the substrate.

Example 4

Determination of the inhibition constant of adenosine-5'-(γ-4-aminophenyl)triphosphate In order to assess the effectiveness of adenosine 5'-(γ-4-aminophenyl)triphosphate as an affinity ligand for protein kinases, the inhibition constants ($K_i$) of the derivative were determined for four different protein kinases, namely, p42$^{mapk}$, cyclic-A kinase, MAPKK and p60$^{c-arc}$ (Table 1). The $K_i$ was determined in the presence of 20 μM ATP. However, since the $K_m$ for ATP varied for each protein kinase tested, for comparative purposes it was convenient to determine the $K_i/K_m$ quotient (Table 1). This also facilitated comparisons for the relative binding constants determined with other ATP analogs (Flockhart et al. (1984) *Eur. J. Biochem.*, 140:289–295; Hoppe et al. (1972) *Eur. J. Biochem.*, 80:369–372; Taylor et al. (1990) *Peptides and Protein Phosphorylation* (Kemp et al.) pp 2–32, CRC Press).

At 20 μM ATP, the apparent $K_i$ values obtained against each enzyme varied over 75–180 μM, with $K_i/K_m$ quotient in the range of 10–20 (Table 1). These results indicate that adenosine-5'-(γ-4-aminophenyl)-triphosphate competes with ATP and that the presence of an aminophenyl moiety linked to the γ phosphate does not adversely affect binding of the nucleotide to these enzymes. This is consistent with ATP binding to cyclic-A kinase, as shown in FIG. 3 in which the γ phosphate is oriented and exposed at the opening of the catalytic cleft. This is also consistent with data demonstrating that exchange of the oxygen of the γ-phosphoryl group for sulfur, did not adversely affect binding of ATP to cyclic-A kinase, phosphorylase kinase or cyclic-GMP-dependent protein kinase ( Flockhart et al. (1984) Supra) .

Generally, increases in the $K_i/K_m$ quotient were observed when substitutions were made at the α and β phosphates or at the hydroxyl and amino moieties of adenosine (Flockhart et al. (1984) Supra). In these studies, no effect on the $K_i$ or $K_i/K_m$ quotient was observed when the [Mg$^{2+}$] was reduced to levels equimolar with free ATP in the protein kinase assays. This suggests that additional Mg$^{2+}$ may not significantly influence the binding of adenosine-5'-(γ-4-aminophenyl)triphosphate to the active site of the protein kinases tested.

TABLE 1

| Protein kinase | μM | | |
|---|---|---|---|
| | $K_i$ ± SDM | $K_m$ATP + SDM | $K_i/K_m$ |
| Cyclic A kinase | 103.60 ± 11.6 | 7.1 ± 0.51 | 14.60 |
| p42$^{mapk}$ | 75.18 ± 8.20 | 7.5 ± 0.71 | 10.02 |
| MAPKK | 176.28 ± 22.1 | 11.3 ± 1.25 | 15.20 |
| p60$^{c-src}$ | 120.00 ± 13.6 | 6.2 ± 1.30 | 19.35 |

Example 5

Use of adenosine-5'-(γ-4-aminophenyl)triphosphate-Sepharose for affinity purification of MAPKK MAPKK is an enzyme which specifically phosphorylates and activates MAPK. Like MAPK, MAPKK is activated by increased phosphorylation. This protein kinase has further been the subject of intense research to discover its mechanism of regulation in vivo. The search of the current protein data bases revealed homology of MAPKK with 4 yeast protein kinases, most notably with Byrl (Nadin-Davis et al. (1988) *EMBO J.*, 7:985–993) and STE7 (Teague et al., (1986) *Proc. Natl. Assoc. Sci.*,83:7371–7375). The deduced amino acid sequence of MAPKK has all of the conserved motifs described above. Sequence alignment of rat kidney MAPKK with cyclic-A kinase reveals the same spacial arrangement of the narrowly invariant amino acids associated with the binding and catalysis of ATP.

Figure 6:
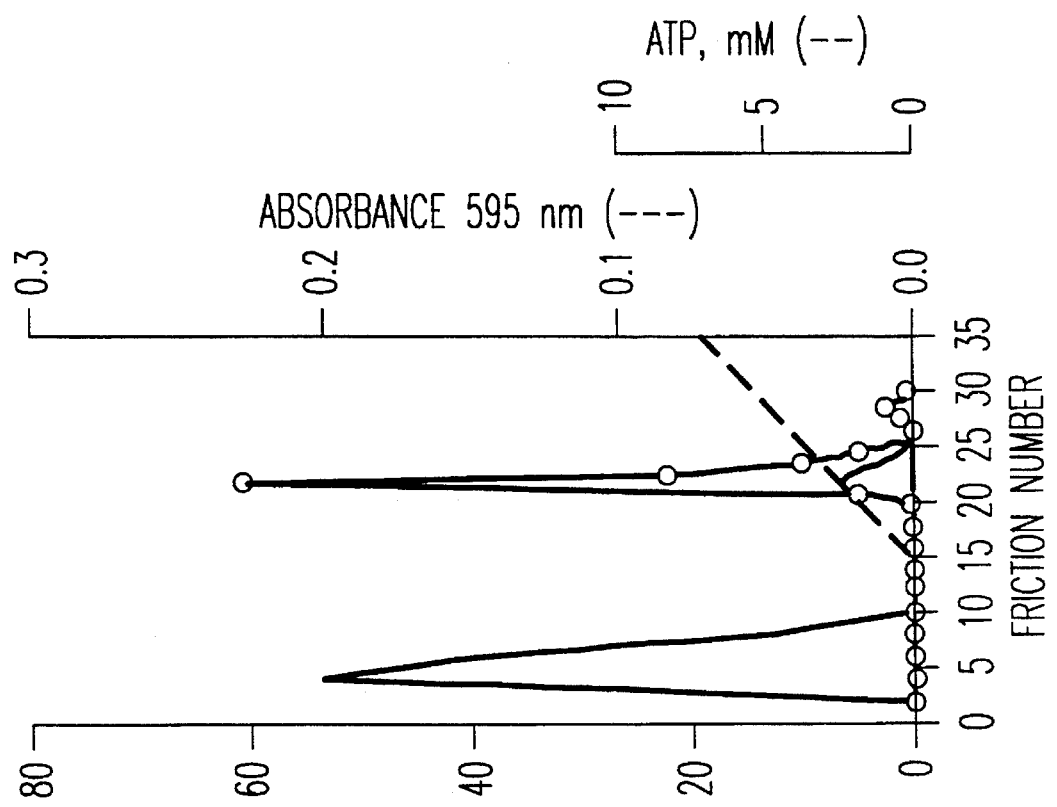
FIG. 6 is a graph of ATP specifically eluted MAPKK from adenosine-5'-(γ-4-aminophenyl)triphosphate-Sepharose showing MAPKK activity versus fraction number.

MAPKK, from rabbit skeletal muscle, was partially purified 600-fold as described earlier (Table 2). Partial purification of the enzyme was necessary to remove other contaminating protein kinases and ATP-binding proteins present in rabbit skeletal muscle homogeniates. Application of extracts to the ATP affinity column at earlier steps in the purification gave preparations of MAPKK which were significantly enriched, but not homogeneous. Partially purified MAPKK was applied to a Waters glass AP-1 column (0.8 cm×10 cm) containing adenosine-5-(γ-4-aminophenyl)triphosphate-Sepharose in solution B containing 60 mM MgCl$_2$ at a flow rate of 0.1 ml/min. The column was developed in this buffer (0.5 ml/min.) and selectively eluted with an increasing ATP gradient of 0 –10 mM. (FIG. 6, Table 2). Column fractions (1.0 ml) were diluted 100-fold with solution B and assayed for MAPKK activity as described in (Haystead et al. 1992). This step enriched the preparation ≈31-fold (Table 2).

TABLE 2

Purification table for MAPKK from rabbit skeletal muscle.
MAPKK was purified through the indicated steps as described in
the Methods. Results shown are from a single experiment, although this was
repeated on a separate occasion with similar results.

| Step | Volume ml | Activity U | Protein mg | Specific activity U/mg | Purifiction -fold | Yield % |
|---|---|---|---|---|---|---|
| Extract | 750 | 5265.0 | 11250.0 | 0.50 | 1.00 | 100.00 |
| DEAE-Cellulose | 4000 | 3948.0 | 805.0 | 4.90 | 9.80 | 75.00 |
| FFQ-Sepharose Waters | 250 | 1381.1 | 102.2 | 13.40 | 26.90 | 26.20 |
| AP-1Q | 20 | 1173.9 | 12.6 | 93.16 | 186.32 | 22.30 |
| G75 Superfine | 6 | 645.6 | 2.1 | 307.45 | 614.90 | 12.26 |
| ATP-Sepharose | 4 | 499.2 | 0.051 | 9788.24 | 19576.50 | 9.49 |

As discussed, adenosine-5-(γ-4-aminophenyl)triphosphate was linked to Sepharose by the carbodiimide reaction. Therefore, potentially some of the derivative may have been N6 linked at the purine ring. This raises the possibility that MAPKK could bind to the column non-specifically through ionic interactions with the α, β and γ phosphates. To ensure that this was avoided, MAPKK was applied to the column in solution B, which contained 50 mM 2-glycerophosphate. The enzyme was therefore selectively eluted from the column by ATP ($\approx$1 mM; FIG. 6). Protein was determined by the method disclosed in Bradford, M. M (1976) *Anal. Biochem.* 72,248–254.

Figure 7A:
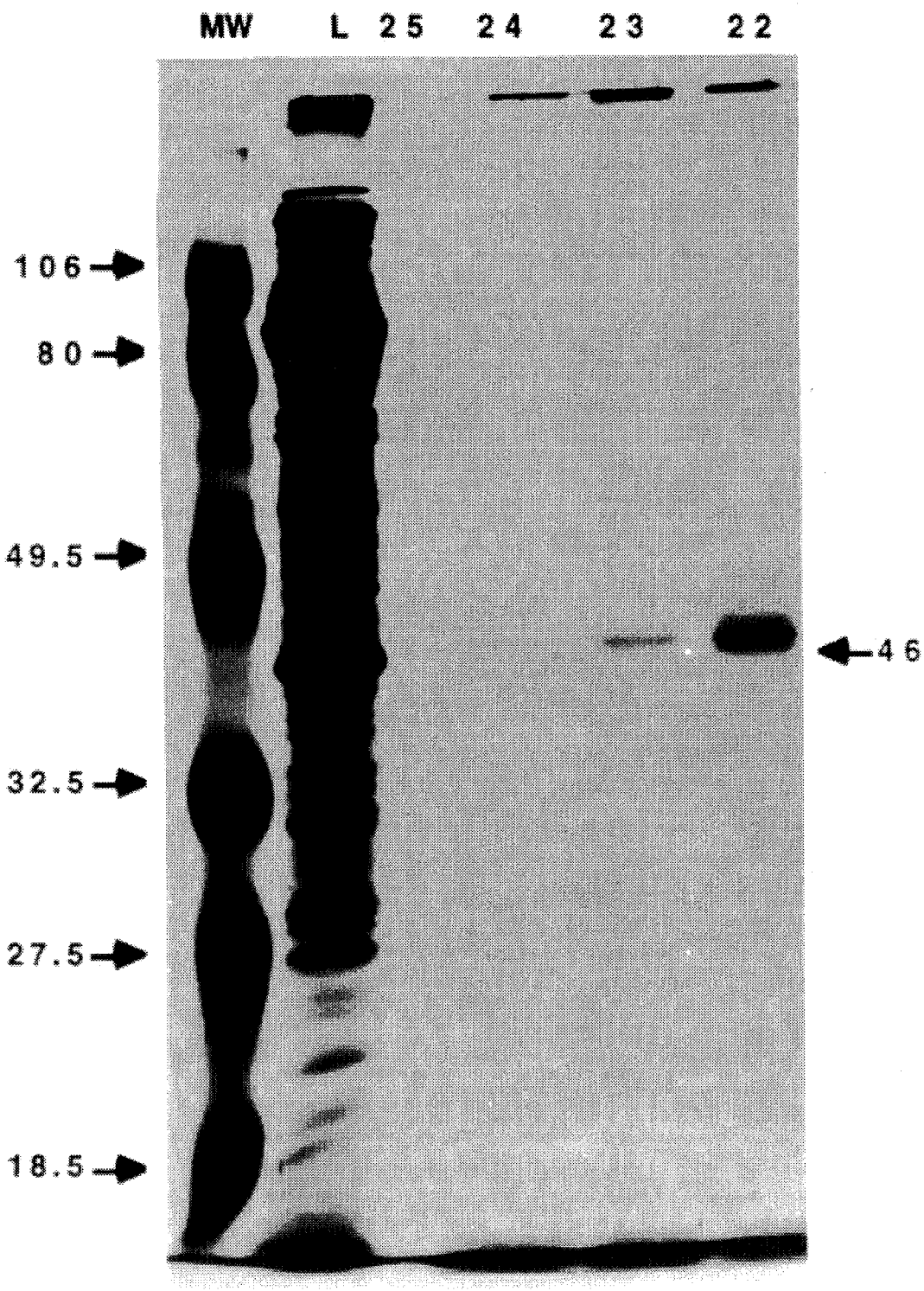
FIG. 7(A) is a silver stain of column fractions from adenosine-5'-(γ-4 -nitrophenyl)triphosphate-Sepharose.
Figure 7B:
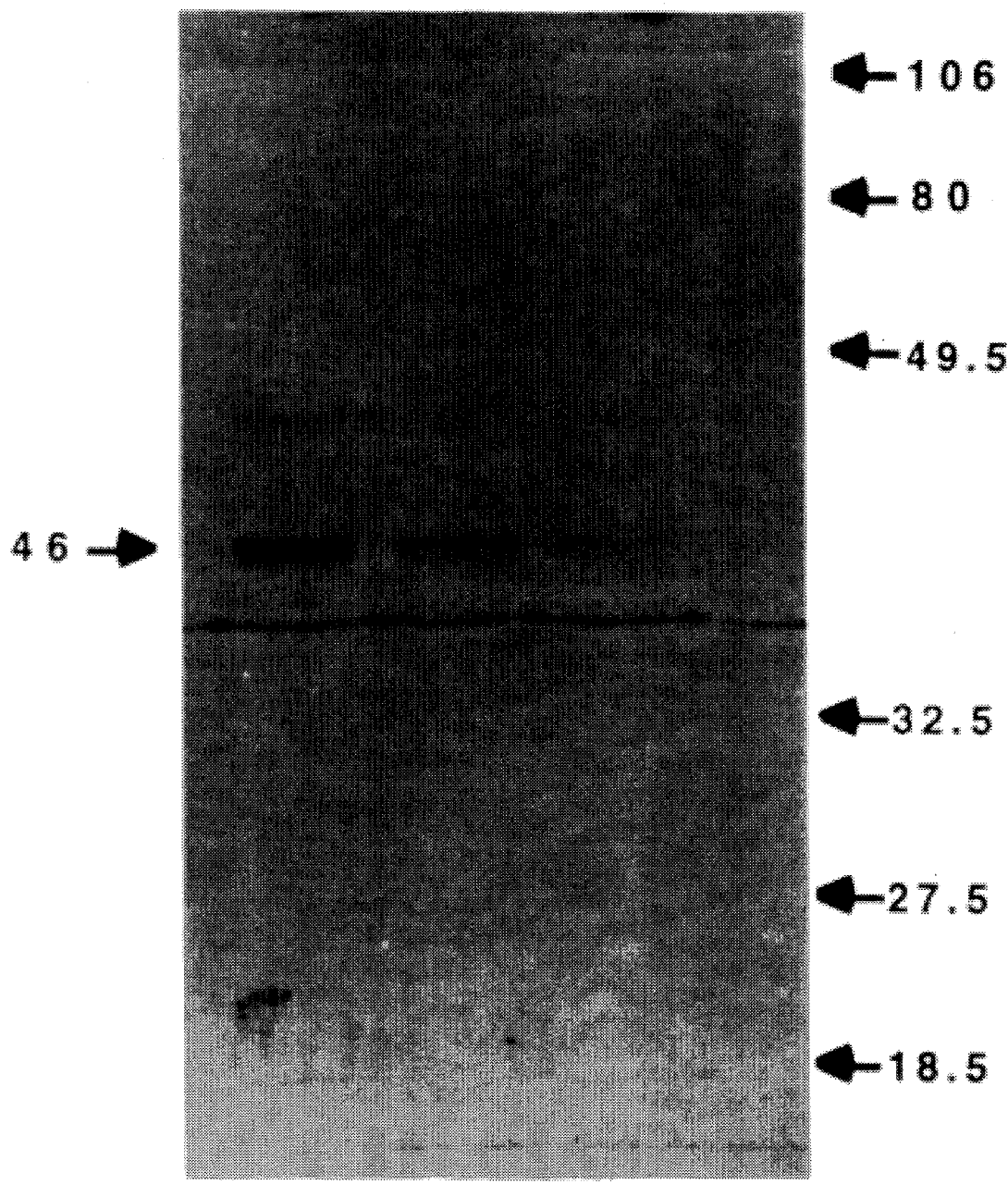
FIG. 7(B) is a western blot of column fractions from adenosine-5'-( γ-4 -nitrophenyl)triphosphate-Sepharose.

Characterization of the peak column fractions of MAPKK activity by SDS/PAGE (6 cm×10 cm gel) and silver staining, revealed the presence of a major staining band at 46 kDa (fraction 22) which represented >98% of the total protein (FIG. 7(A) in which 0.1 ml fractions were measured). Two minor contaminants, at 46.5 kDa and 48.5 kDa, were also present in the fractions, although by silver staining, these represented <2.0% of the total protein. Western blotting of the column fractions with anti-STE7 serum as described in Haystead, T.A.J. et al., (1992) *FEBS Lett.*, 306:1722, showed cross-reactivity with the 46-kDa protein, confirming its identity as MAPKK (FIG. 7(B) in which 0.025 ml fractions were analyzed). The band running at $\approx$36 kDa in FIG. 7, is a staining artifact which was found in all lanes, including those into which no protein was loaded.

From 300 g rabbit skeletal muscle, $\approx$19000-fold purification of MAPKK was required to achieve homogeneity. The use of γ-phosphate-linked ATP-Sepharose yields a homogenous preparation of MAPKK following only 3 chromatographic steps (Table 2).

In previously reported preparations of MAPKK reported by others, such as Nakiehy et al. (1992) *FEBS Lett.*, 308:183–189; Segar et al. (1992) *J. Biol. Chem.*, 267:14373–14381, and Crews et al. 1992 *Science*, 258: 478–480, significantly larger amounts of tissue and up to 10 separate chromatographic steps were required to purify the enzyme, with typical yields of only 1.0–1.5%, these previous attempts yielded a <two-fold purification of MAPKK. This relatively poor purification step is typical of many past protein kinase purification protocols using N6 purine or hydroxyl ribose-linked ATP columns. As discussed, because of the orientation of MgATP within the catalytic cleft of cyclic A kinase (FIG. 3), linkage of ATP through a moiety other than the γ phosphate, would be likely to sterically preclude binding to the catalytic cleft of protein kinases. Thus, previous ATP columns have functioned for the greater part, as weak cation-exchange resins and not as specific affinity ligands for protein kinases.

The following claims are not designed to limit the scope of the subject matter of the present invention. Applicant has endeavored to illustrate their invention by extensive embodiment of possible combinations. Nonetheless, it is recognized that the possible combinations are endless, and cannot be exhaustively embodied. Given the above teaching, those of ordinary skill in the art will arrive at enhancement agents and additives not specifically exemplified in the foregoing application. The examples are not intended to be limiting, and the identification of other combinations, given the foregoing disclosure, is well within the skill of those practicing this technology without undue experimentation. Such combinations are intended to be within the scope of the invention, save as expressly limited or excluded by the claims set forth below.

What is claimed is:

1. A γ-phosphate linked ATP affinity column for purification of protein kinases comprising:

a) a solid support; and b) a linking moiety linked to said solid support, wherein said linking moiety has the following formula:

—X—Y—Z—(Q)$_3$-adenosine, wherein X is a straight or branched chain having at least 6–9 carbon atoms and is suitable for covalently linking —Y—Z—(Q)$_3$ adenosine to said solid support; Y is selected from the group consisting of an amino, nitro, hydroxyl, and disulfo group; Z is a phenyl group; and Q is phosphate or thiophosphate, wherein said affinity column reversibly binds protein kinases introduced thereto.

2. The affinity column of claim 1, when said solid support is selected from the group consisting of Sepharose, agarose gels, cross-linked agarose gels, controlled-pore glass beads, cellulose particles, and polyacrylamide gel beads.

3. The affinity column of claim 2, wherein said solid support is Sepharose.

4. The affinity column of claim 1, wherein X provides an aldehyde linkage to —Y—Z—(Q)$_3$-adenosine.

5. The affinity column of claim 1, wherein Y is selected from the group consisting of an amino and nitro group.

6. The affinity column of claim 1, when Z is phenylene.

7. The affinity column of claim 1, when Q is phosphate.

* * * * *

UNITED STATES PATENT AND TRADEMARK OFFICE
CERTIFICATE OF CORRECTION

PATENT NO. : 5,536,822  
DATED : July 16, 1996  
INVENTOR(S) : Timothy A. J. Haystead It is certified that error appears in the above-identified patent and that said Letters Patent is hereby corrected as shown below:

Column 1,
Line 3, the following paragraph is inserted after the title:
-- U.S. Government Rights
This invention was made with United States Government support under Grant No. HL19242, awarded by the National Institutes of Health. The United States Government has certain rights in the invention. --

Signed and Sealed this

Sixth Day of July, 2004

JON W. DUDAS  
*Acting Director of the United States Patent and Trademark Office*